US007071382B2

(12) United States Patent
Cahoon et al.

(10) Patent No.: US 7,071,382 B2
(45) Date of Patent: Jul. 4, 2006

(54) INHIBITORS OF APOPTOSIS PROTEINS IN PLANTS

(75) Inventors: Rebecca E. Cahoon, Webster Grove, MO (US); Perry G. Caimi, Kennett Square, PA (US); Theodore M. Klein, Wilmington, DE (US); Michele Morgante, Wilmington, DE (US); Hajime Sakai, Newark, DE (US); Jennie Bih-Jien Shen, Wilmington, DE (US); Scott V. Tingey, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 97 days.

(21) Appl. No.: 10/679,998

(22) Filed: Oct. 7, 2003

(65) Prior Publication Data

US 2004/0111767 A1    Jun. 10, 2004

Related U.S. Application Data

(63) Continuation of application No. 09/601,929, filed as application No. PCT/US99/05227 on Mar. 10, 1999, now abandoned.

(60) Provisional application No. 60/078,144, filed on Mar. 16, 1998.

(51) Int. Cl.
  *A01H 1/00*     (2006.01)
  *C07H 21/04*    (2006.01)
  *C07K 14/415*   (2006.01)
  *C12N 5/14*     (2006.01)
  *C12N 9/00*     (2006.01)

(52) U.S. Cl. .................... 800/295; 435/6; 435/69.1; 435/468; 435/419; 435/252.3; 435/320.1; 435/183; 530/370; 536/23.6; 800/278

(58) Field of Classification Search .................. 435/6, 435/69.1, 468, 419, 252.3, 320.1, 183; 530/370; 536/23.6; 800/278, 296
See application file for complete search history.

(56) References Cited

U.S. PATENT DOCUMENTS 6,162,965 A    12/2000  Hansen

FOREIGN PATENT DOCUMENTS

EP          0892 048 A    1/1999

OTHER PUBLICATIONS

Bork, P. Genome Research. vol. 10, 2006, p. 398-400.*
Lazar et al. Molecular & Cellular Biology, Mar. 1988 vol. 8, No. 3, p. 1247-1252.*
Burgess et al. The Journal of Cell Biology, 1990 vol. III, p. 2129-2138.*
Brown et al. Science, Nov. 13, 1998, vol. 282, p. 131-133.*
Yoshikazu Tanaka et al., dad-1, A putative programmed cell death suppressor gene in rice, Plant Cell Physiol., 1997, vol. 38(3):379-383.
Patrick Gallois et al., An *Arabidopsis thaliana* cDNA complementing a hamster apoptosis suppressor mutant, Plant Journal, 1997, vol. 11(6):1325-1331.
Diego Orzaez et al., The plant homologue of the defender against apoptotic death gene is down-regulated during senescence of flower petals, FEBS Letters, 1997, vol. 404:275-278.
Suneel S. Apte et al., The highly conserved defender against the death 1 (DAD1) gene maps to human chromosome 14q11-q12 and mouse chromosome 14 and has plant and nematode homologs, FEBS Letters, 1995, vol. 363:304-306.
Asako Sugimoto et al., dad-1, an endogenous programmed cell death suppressor in *Caenorhabditis elegans* and vertebrates, EMBO J., 1995, vol. 14(18):4434-4441.
Daniel J. Kelleher et al., dad1, the defender against apoptotic cell death, is a subunit of the mammalian oligosaccharyltransferase, Proc. Natl. Acad. Sci., May 1997, vol. 94:4994-4999.
Alison J. Mastrangelo et al., Overcoming apoptosis: new methods for improving protein-expression systems, 1998, vol. 16:88-95.
V.S. Vysotskaia et al., The sequence of BAC F21M12 from *Arabidopsis thaliana* chromosome 1, EMBL Sequence Data Library, Mar. 19, 1997, Accession No. AC000132.
D. L. Carson et. al., Sugarcane cDNA from leaf roll tissue, EMBL Sequence Data Library, Oct. 16, 1996, Accession No. AA 080664.
O. Chao et al., Genomic sequences for *Arabidopsis thaliana* BAC F17F8, EMBL Sequence Data Library, Jan. 30, 1997, Accession No. AC000107.
C.O. Lim et al., Generation of expressed sequence tags from random sequencing of chinese cabbage (*Brassica campestris* L. ssp. Pekinensis) flower bud cDNA clones, EMBL Sequence Data Library. Sep. 5, 1995, Accession No. L46557.

(Continued)

*Primary Examiner*—Phuong T. Bui
(74) *Attorney, Agent, or Firm*—E. I. du Pont de Nemours and Company

(57) ABSTRACT

This invention relates to an isolated nucleic acid fragment encoding an apoptosis inhibitory protein. The invention also relates to the construction of a chimeric gene encoding all or a portion of the apoptosis inhibitory protein, in sense or antisense orientation, wherein expression of the chimeric gene results in production of altered levels of the apoptosis inhibitory protein in a transformed host cell.

12 Claims, 3 Drawing Sheets

OTHER PUBLICATIONS

M. Bevan et al., Analysis of 1.9 Mb of Contiguous Sequence from Chromosome 4 of *Arabidopsis thaliana*, Nature, Jan. 29, 1998, 391:485-488.

P. Liston et al., Suppression of apoptosis in mammalian cells by NAIP and a related family of IAP Genes, Nature, Jan. 25, 1996, vol. 379(6563):349-353.

Q. L. Deveraux et al., X-Linked IAP is a Direct Inhibitor of Cell-Death Proteases, Nature, Jul. 17, 1997, vol. 388:300-304.

Herman Steller, Artificial death switches: Induction of apoptosis by chemically induced caspase multimeriaztion, Proc. Natl. Acad. Sci., May 1998, vol. 95:5421-5422.

National Center for Biotechnology Information General Identifier No. 2723473, Accession No. D89726, Jun. 8, 1998, Yoshikazu Tanaka et al., dad-1, A putative programmed cell death gene in rice.

National Center for Biotechnology Information General Identifier No. 2623638; Accession No. AF030172, Apr. 17, 1998, A. Danon et al., AtDAD2: A new gene from the DAD1 family in Arabidopsis.

National Center for Biotechnology Information General Identifier General Identifier No. 2623761. Accession No. U83857, Apr. 17, 1998, M. Tewari, AAC-11, A novel cDNA that inhibits apoptosis after growth factor withdrawl.

National Center for Biotechnology Information General Identifier No. 3869255, Accession No. U79562, Nov. 13, 1998, D. Orzaez et al., The plant homologue of the defender against apoptotic death gene is down-regulated during senescence of flower petals.

National Center for Biotechnology Information General Identifier No. 3608136, Accession No. AC005314, Nov. 23, 1998, S. D. Rounsley et al., *Arabidopsis thaliana* chromosome II BAC T32F-12 genomic sequence.

P. Liston et al. Life and death decisions: the role of the IAPs in modulating programmed cell death, Apoptosis 1997, 2:423-441.

* cited by examiner

```
                                1                                                           60
SEQ ID NO:13    MV------KSTSKDAQDLFHSLHSAY-TATPTNLKIIDLYVCFAVFTALIQVAYMALVGS
SEQ ID NO:14    MP------RATSDAKLLIQSLGKAY-AATPTNLKIIDLYVVFAVATALIQVVYMGIVGS
SEQ ID NO:15    MA------KTSSTTKDAQDLFHAIWSAY-SATPTNLKIIDLYVVFAVFTALLQDVYMALVGP
SEQ ID NO:2     MA------RSSSKDAQDLFRALWSAY-AATPTNLKIIDLYVMFAVFTALIQVVYMALVGS
SEQ ID NO:4     MP------RATSDAKLLIQSLGKAY-AATPTNLKIIDLYVGFAVATALIQVAYMGLVGS
SEQ ID NO:6     MA------PRSSSKDAQDLFRALWSAY-AATPTNLKIIDLYVIYAVFTAFIQVVYMALVGS 61                                                          120
SEQ ID NO:13    FPFNSFLSGVLSCIGTAVLAVCLRIQVNKENK-EFKDLAPERAFADFVLCNLVLHLVIIN
SEQ ID NO:14    FPFNSFLSGVLSCIGTAVLAVCLRIQVNKDNK-EFKDLPPERAFADFVLCNLVLHLVIMN
SEQ ID NO:15    FPFNSFLSGVLSCVGTAVLAVCLRIQVNKENK-EFKDLGPERAFADFVLCNLVLHLVIMN
SEQ ID NO:2     FPFNSFLSGVLSCIGTAVLAVCLRIQVNKENK-EFKDLAPERAFADFVLCNLVLHLVIMN
SEQ ID NO:4     FPFNSFLSGVLSCIGTAVLAVCLRIQVNKDNK-EFKDLPPERAFADFVLCNLVLHLVIMN
SEQ ID NO:6     FPFNSFLSGVLSCVGTAVLAVCLRIQVNKENK-EFKDLAPERAFADFVLCNLVLHLVIMN

121
SEQ ID NO:13    FL-G
SEQ ID NO:14    FL-G
SEQ ID NO:15    FLG.
SEQ ID NO:2     FLG.
SEQ ID NO:4     FLG.
SEQ ID NO:6     FLG.
```

FIG. 1

```
SEQ ID NO:16        1  MGLSLT--MPTVEELYRNYGILADATEQVGQHKDAYQVILDGVKG-GTKEKRLAAQFIPK         60
SEQ ID NO:8            MAAAAADDAAEVERLY-ELGERLSSANDKSEHAADYEAIIAAVKGQSAKAKQLAAQLIPR

SEQ ID NO:16       61  FFKHFPELADSAINAQLDLCEDEDVSIRRQAIKELPQF--ATGENLPRVADILTQLLQTD        120
SEQ ID NO:8            FFRSFPALGTRAMSAMFDLVDMEELAIRIQAIRGFPLLGKDT-EFVSKIADVLGQLLTSE

SEQ ID NO:16      121  DSAEFNLVNNALLSIFKMDAKGTLGGLFSQIL---QGEDIVRERAIKFLSTKLKTLPDEV        180
SEQ ID NO:8            ENVERDAVHKALMSLIRQDVKNSLQPLFKHVE----QGSEIREKIICFLRDKVFPLKAEL

SEQ ID NO:16      181  LT--KEVEELILTESKKVLEDVTGEEFVLFMKILSGLKSLQTVSGR---QQLVELVAEQA        240
SEQ ID NO:8            LKPQAEMERFITDLIKKSVQDVTGSEFELFMGFLRXWSIFGDSAPRESFQELIEIIQAQA

SEQ ID NO:16      241  DLEQTFNPSDPDCVDRLLQCTRQAVPLFSKNVHSTRFVTYFCEQVLPNLGTLTTPVEGLD        300
SEQ ID NO:8            DLNSQFNVSDIDHIERWISCMYMALPIFMRGASASKFLNYFVKQIVPAFEKIPE----E

SEQ ID NO:16      301  IQLEVLKLLAEMSSFCGDMEKLETNLRKLFDKLLEYMPLPPEEAAENGENAGNEEPKLQFS        360
SEQ ID NO:8            KKLDLLKTIASSSPYATAQDSRQL-LPSVVQLLNKYMP-------GKKV-DD---INHN
```

FIG. 2A

```
             361                                                       420
SEQ ID NO:16  YVECLLYSFHQLGRKLPDFLTA----KL-----NAEKLHES-------KIRLQYFARGLQ
SEQ ID NO:8   YVECLLYTYHHLAHKTPNTTNSLCGYKIVTGQPSDRLGEDFTEHYKDFTERLTGTEETVR 421                                                       480
SEQ ID NO:16  VYIRQLRLALQG--KTGEALKTEENKIKV-------VALKITNNINVLIKDLFHIPPSY
SEQ ID NO:8   AASKRLTQGMADFSKAISSAKTEEEKTKIKGDQQTSTRTMRSYNNILAMTQSLHSKSPLF 481                                                       540
SEQ ID NO:16  --KSTVTLSW----KPVQKVEIGQKRASEDTTSGSPPKKSSAGPKRMPGRFITLPVGNIA
SEQ ID NO:8   IGDKKITTLSWMEQPNKAAATKAGGKRSQPSTNGNDPANKKGRGG--MQNQLVNRAFEGLS 541                                       588
SEQ ID NO:16  AIWATLIMRGAFRGSK---------WPRLGH--TKEIVVGERLY
SEQ ID NO:8   HVGRGSGRXRGXGGPRKRKRMEWGTTEMTWKLCSNLTRDELSASTRE.
```

INHIBITORS OF APOPTOSIS PROTEINS IN PLANTS

This application is a continuation of U.S. Pat. application 09/601,929, filed Aug. 9, 2000, now abandoned, which was a 35 U.S.C. 371 filing of PCT International Application PCT/US99/05227, filed Mar. 10, 1999, now expired, which claims priority to U.S. Provisional Application Ser. No. 60/078,144, filed Mar. 16, 1998, now expired.

FIELD OF THE INVENTION

This invention is in the field of plant molecular biology. More specifically, this invention pertains to nucleic acid fragments encoding proteins that inhibit apoptosis in plants and seeds.

BACKGROUND OF THE INVENTION

Multicellular organisms have evolved elaborate signal transduction pathways for maintaining homeostasis through the control of cell proliferation and death. Programmed cell death or apoptosis is a process in which unwanted cells are eliminated during growth and development (Steller, H. (1998) *PNAS* 95:5421–5422). Inhibitors of apoptosis proteins (IAPs) constitute a family of highly conserved death-suppressing proteins that were first identified in baculoviruses (Liston, P. et al. (1997) *Apoptosis* 2(5):423–441). Two homologues have been identified in *Drosophila melanogaster* (D-IAP and D-IAP-2) and several in rodents and humans including human AAC-11 protein, X-linked inhibitor of apoptosis, XIAP and an XIAP associated protein ZAP-1 (Liston, P. et al. (1997) *Apoptosis* 2(5):423–441 and Liston, P. et al. (1996) *Nature* 379:349–352). Several DAD1 (defender against death) proteins have also been identified in mammalian and plant cells (Gallosis, P. et al. (1997) *Plant J.* 11(6):1325–1331). These proteins appear to be a subunit of oligosaccharyltransferase (OST), an enzyme that is involved in N-linked glycosylation in eukaryotes and may also be associated with programmed cell death in mammalian and plant cells. No genes encoding IAP, IAP-2, ZAP-1 or AAC-11 proteins in plants, especially corn, rice soybean and wheat, have been isolated and sequenced.

There is a great deal of interest in identifying the genes that encode IAPs in plants. These genes may be used to express IAPs in plant cells to enhance cell tissue culture growth. Accordingly, the availability of nucleic acid sequences encoding all or a portion of IAPs would facilitate studies to better understand programmed cell death in plants, provide genetic tools to enhance cell growth in tissue culture, increase the efficiency of gene transfer and help provide more stable transformations.

SUMMARY OF THE INVENTION

The instant invention relates to isolated nucleic acid fragments encoding proteins that inhibit apoptosis. Specifically, this invention concerns an isolated nucleic acid fragment encoding a DAD1 or AAC-11 protein. In addition, this invention relates to a nucleic acid fragment that is complementary to the nucleic acid fragment encoding a DAD1 or AAC-11 protein.

An additional embodiment of the instant invention pertains to a polypeptide encoding all or a substantial portion of an apoptosis inhibitory protein selected from the group consisting of DAD1 and AAC-11.

In another embodiment, the instant invention relates to a chimeric gene encoding a DAD1 or AAC-11 protein, or to a chimeric gene-that comprises a nucleic acid fragment that is complementary to a nucleic acid fragment encoding a DAD1 or AAC-11 protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a DAD1 or AAC-11 protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a DAD1 or AAC-11 protein in a transformed-host cell comprising: a) transforming a host cell with a chimeric gene comprising a nucleic acid fragment encoding a DAD1 or AAC-11 protein; and b) growing the transformed host cell under conditions that are suitable for expression of the chimeric gene wherein expression of the chimeric gene results in production of altered levels of DAD1 or AAC-11 protein in the transformed host cell.

An addition embodiment of the instant invention concerns a method for obtaining a nucleic acid fragment encoding all or a substantial portion of an amino acid sequence encoding a DAD1 or AAC-11 protein.

BRIEF DESCRIPTION OF THE FIGURES AND SEQUENCE LISTINGS

The invention can be more fully understood from the following detailed description and the accompanying Sequence Listing which form a part of this application.

FIG. 1 shows a comparison of the amino acid sequences of the *Arabidopsis*, rice and pea DAD1 proteins (SEQ ID NO:13, SEQ ID NO:14 and SEQ ID NO:15, respectively) and SEQ ID NOs:2, 4 and 6.

FIGS. 2A and 2B show a comparison of the amino acid sequences of the human AAC-11 protein (SEQ ID NO:16) and SEQ ID NO:8.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone plht.pk0012.c8 encoding a *Phaseolus* DAD1 protein.

SEQ ID NO:2 is the deduced amino acid sequence of an entire DAD1 protein derived from the nucleotide sequence of SEQ ID NO:1.

SEQ ID NO:3 is the nucleotide sequence comprising the entire cDNA insert in clone cbn10.pk0058.g12 encoding a corn DAD1 protein.

SEQ ID NO:4 is the deduced amino acid sequence of an entire DAD1 protein derived from the nucleotide sequence of SEQ ID NO:3.

SEQ ID NO:5 is the nucleotide sequence comprising a contig assembled from the cDNA inserts in clones sls1c.pk010.h9, ses2w.pk0011.h3, sdp4c.pk007.e17, se1.pk0035.e10 and sl1.pk0106.d1 encoding a soybean DAD1 protein.

SEQ ID NO:6 is the deduced amino acid sequence of an entire DAD1 protein derived from the nucleotide sequence of SEQ ID NO:5.

SEQ ID NO:7 is the nucleotide sequence comprising a contig assembled from the cDNA inserts in clones p0031.ccmba65r, p0037.crwaj44r, p0049.curar45r, p0004.cb1ha38r, p0011.cdapf47r, cbn10.pk0041.h3, cen1.pk0032.d4 and p0116.cesag38r encoding a corn AAC-11 protein.

SEQ ID NO:8 is the deduced amino acid sequence of an entire AAC-11 protein derived from the nucleotide sequence of SEQ ID NO:7.

SEQ ID NO:9 is the nucleotide sequence comprising a portion of the cDNA insert in clone rls24.pk0025.b4 encoding a rice AAC11 protein.

SEQ ID NO:10 is the deduced amino acid sequence of a portion of an AAC-11 protein derived from the nucleotide sequence of SEQ ID NO:9.

SEQ ID NO:11 is the nucleotide sequence comprising a contig assembled from the cDNA inserts in clones sdp2c.pk027.j3 and src3c.pk001.j10 encoding a soybean AAC-11 protein.

SEQ ID NO:12 is the deduced amino acid sequence of a portion of a AAC-11 protein derived from the nucleotide sequence of SEQ ID NO:11.

SEQ ID NO:13 is the amino acid sequence of the *Arabidopsis thaliana* DAD1 protein set forth in NCBI Identifier No. gi 2623638.

SEQ ID NO:14 is the amino acid sequence of the *Oryza sativa* DAD1 protein set forth in NCBI Identifier No. gi 2723473.

SEQ ID NO:15 is the amino acid sequence of the *Pisum sativum* DAD1 protein set forth in NCBI Identifier No. gi 3869255.

SEQ ID NO:16 is the amino acid sequence of the *Homo sapiens* AAC-11 protein set forth in NCBI Identifier No. gi 2623761.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules. set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence. As used herein a "peptide", "polypeptide" or protein refers to a linear polymer composed of amino acids connected by peptide bonds.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 85% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M.

(1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Blot* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g.. in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The Instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the DAD1 or AAC-11 proteins as set forth in SEQ ID NOs:2, 4, 6, 8, 10, 12, 14, 16 and 18. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (*London*) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several apoptosis inhibitory proteins have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Apoptosis Inhibitory Proteins

| Enzyme | Clone | Plant |
| --- | --- | --- |
| Defenders against cell death protein DAD1 | plht.pk0012.c8 | Lima bean |
| | cbn10.pk0058.g12 | Maize |
| | sls1c.pk010.h9 | Soybean |
| | ses2w.pk0011.h3 | Soybean |
| | sdp4c.pk007.e17 | Soybean |
| | se1.pk0035.e10 | Soybean |
| | sl1.pk0106.d1 | Soybean |
| Inhibitor of Apoptosis Protein AAC-11 | p0031.ccmba65r | Corn |
| | p0037.crwaj44r | Corn |
| | p0049.curar45r | Corn |
| | p0004.cblha38r | Corn |
| | p0011.cdapf47r | Corn |
| | cbn10.pk0041.h3 | Corn |
| | cen1.pk0032.d4 | Corn |
| | p0116.cesag38r | Corn |
| | rls24.pk0025.b4 | Rice |
| | sdp2c.pk027.j3 | Soybean |
| | src3c.pk001.j10 | Soybean |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other DAD1 or AAC-11 protein, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohmnan et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed DAD1 or AAC-11 proteins are present at higher or lower levels than normal or in cell types or developmental stages in which they are not normally found. This would have the effect of altering the level of DAD1 or AAC-11 proteins in those cells. Altering the level of DAD1 and AAC-11 proteins in cells could facilitate studies to better understand programmed cell death in plants, provide genetic tools to alter programmed cell death, enhance cell growth in tissue culture, increase the efficiency of gene transfer and help provide more stable transformations.

Overexpression of the DAD1 or AAC-11 proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant apoptosis inhibitory proteins to different cellular compartments, or to facilitate its secretion from the cell. It is thus envisioned that the chimeric gene described above may be further supplemented by altering the coding sequence to encode a DAD1 or AAC-11 protein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding DAD1 or AAC-11 proteins in plants for some applications. In order to accomplish this, a chimeric gene designed for co-suppression of the instant apoptosis inhibitory proteins can be constructed by linking a gene or gene fragment encoding a DAD1 or AAC-11 protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant DAD1 or AAC-11 proteins (or portions thereof) may be produced in heterologous host cells, particularly in the cells of microbial hosts, and can be used to prepare antibodies to the these proteins by methods well known to those skilled in the art. The antibodies are useful for detecting DAD1 or AAC-11 proteins in situ in cells or in vitro in cell extracts. Preferred heterologous host cells for production of the instant DAD1 or AAC-11 proteins are microbial hosts. Microbial expression systems and expression vectors containing regulatory sequences that direct high level expression of foreign proteins are well known to those skilled in the art. Any of these could be used to construct a chimeric gene for production of the instant DAD1 or AAC-11 proteins. This chimeric gene could then be introduced into appropriate microorganisms via transformation to provide high level expression of the encoded apoptosis inhibitory protein. An example of a vector for high level expression of the instant DAD1 or AAC-11 proteins in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1): 37–41. Numerous publications describe genetic mapping of specific cDNA clones using the methodology outlined above or variations thereof For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the DAD1 or AAC-11 protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a DAD1 or AAC-11 protein can be identified and obtained. This mutant plant can then be used to determine or confirm the natural function of the DAD1 or AAC-11 protein gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, *Phaseolus* and soybean tissues were prepared. The characteristics of the libraries are described below.

TABLE 2 cDNA Libraries from Corn, Rice, Phaseolus and Soybean

| Library | Tissue | Clone |
| --- | --- | --- |
| cbn10 | Corn developing kernel (embryo and endosperm; 10 days after pollination) | cbn10.pk0058.g12 cbn10.pk0041.h3 |
| cen1 | Corn endosperm 11 days after pollination | cen1.pk0032.d4 |
| p0031 | Corn shoot culture, initiated from seed derived meristems | p0031.ccmba65r |
| p0037 | Corn, V5 roots, infested with corn root worm | p0037.crwaj44r |
| p0049 | Corn, 5 days after pollination, whole kernels | p0049.curar45r |
| p0004 | Corn immature ear | p0004.cb1ha38r |
| p0011 | Corn, 5 days after pollination whole kernels | p0011.cdapf47r |
| p0116 | Corn, DAM methylase induced transgenic suspension cells* | p0116.cesag38r |
| plht | *Phaseolus lunatus* leaf-heat tolerant | plht.pk0012.c8 |
| rls24 | Rice leaf (15 days after pollination) 24 hours after infection of *Magaporthe grisea* strain 4360-R-67 (avr2-yamo); Susceptible | rls24.pk0025.b4 |
| sdp4c | Soybean (*Glycine max* L.) developing embryo (9–11 mm) | sdp4c.pk007.e17 |
| sdp2c | Soybean (*Glycine max* L.) developing pods 6–7 mm | sdp2c.pk027.j3 |
| ses2w | Soybean (*Glycine max* L.) embryogenic suspension 2 weeks after subculture | ses2w.pk0011.h3 |
| se1 | Soybean (*Glycine max* L.) embryo, 6–10 days after flowering | se1.pk0035.e10 |
| sl1 | Soybean (*Glycine max* L.) two week old developing seedlings treated with water | sl1.pk0106.d1 |
| sls1c | Soybean (*Glycine max* L., S1990) infected with *Sclerotinia sclerotiorum* mycelium | sls1c.pk010.h9 |
| src3c | Soybean (*Glycine max* L., Bell) 8 day old root inoculated with eggs of cyst nematode *Heterodera glycines* (Race 14) for 4 days | src3c.pk001.j10 |

*Cell line is transgenic for a vector harboring four copies of the estrogen response element (ERE) and CaMV +59 promoter driving dam methylase expression (Klein-Hitpab, L., et al., (1989) Cell 46: 1053–1061). Expression of dam methylase was induced by 17 alpha-ethnylestradiol.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding apoptosis Inhibitory proteins were identified by conducting BLAST (Basic Local Alignment Search Tool; Altschul, S. F., at al., (1993) *J. Mol. Biol.* 215: 403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish. W. and States, D. J. (1993) *Nature Genetics* 3:266–272 and Altschul, Stephen F., et al. (1997) *Nucleic Acids Res.* 25:3389–3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding DAD1 Homologs

The BLASTX search using the EST sequences from clones plht.pk0012.c8 and se1.pk0035.e10 revealed similarity of the proteins encoded by the cDNAs to DAD1 from *Arabidopsis thaliana* (NCBI Identifier No. gi 3608136). Subsequently, several other soybean clones (sls1c.pk010.h9, ses2w.pk0011.h3, sdp4c.pk007.e17 and sl1.pk0106.d1) were obtained that had similarity of the proteins encoded by the cDNAs to DAD1 from *Arabidopsis thaliana* (NCBI Identifier No. gi 3608136) and *Pisum sativum* (NCBI Identifier No. gi 3869255). In the process of comparing the soybean clones it was found that they had overlapping regions of homology. Using this homology it was possible to align all the soybean clones, including se1.pk0035.e10, in order to assemble a contig encoding a unique soybean DAD1 protein. The assembled contig revealed similarity of the encoded protein to DAD1 from *Pisum sativum* (NCBI Identifier No. gi 3869255). The BLASTX search using EST sequence from a corn clone, cbn10.pk0058.g12, revealed similarity of the protein encoded by the cDNA to DAD1 from *Oryza saliva* (NCBI Identifier No. gi 2723473). The BLAST results for the corn and *Phaseolus* ESTs and the soybean contig are shown in Table 3:

TABLE 3

BLAST Results for Clones Encoding Polypeptides Homologous to *Arabidopsis thaliana* DAD1 Proteins

| Clone | BLAST pLog Score |
| --- | --- |
| plht.pk0012.c8 | 64.00 |
| cbn10.pk0058.g12 | 67.30 |
| Contig composed of:<br>se1.pk0035.e10<br>ses2w.pk0011.h3<br>sdp4c.pk007.e17<br>sl1.pk0106.d1<br>sls1c.pk010.h9 | 62.00 |

The sequence of the cDNA insert in clone plht.pk0012.c8 encodes 100% of a *Phaseolus* DAD1 protein and is shown in SEQ ID NO:1; the deduced amino acid sequence of this cDNA is shown in SEQ ID NO:2. The amino acid sequence set forth in SEQ ID NO:2 was evaluated by BLASTP, yielding a pLog value of 53.00 versus an *Arabidopsis thaliana* (NCBI Identifier No. gi 2623638) DAD1 sequence. A calculation of the percent similarity of the amino acid sequence set forth in SEQ ID NO:2 and the *Arabidopsis thaliana* sequence can be seen in Table 4.

The sequence of the entire cDNA insert in clone cbn10.pk0058.g12 was determined and is shown in SEQ ID NO:3; the deduced amino acid sequence of this cDNA is shown in SEQ ID NO:4. The amino acid sequence set forth in SEQ ID NO:4 was evaluated by BLASTP, yielding a pLog value of 57.00 versus the *Oryza sativa* (NCBI Identifier No. gi 2723473) sequence. A calculation of the percent similarity of the amino acid sequence set forth in SEQ ID NO:4 and the *Oryza sativa* sequence can be seen in Table 4.

The sequence of the entire contig composed of clones se1.pk0035.e10, ses2w.pk0011.h3, sdp4c.pk007.e17, sl1.pk0106.d1 and sls1c.pk010.h9 is shown in SEQ ID NO:5; the deduced amino acid sequence of this cDNA is shown in SEQ ID NO:6. The amino acid sequence set forth in SEQ ID NO:6 was evaluated by BLASTP, yielding a pLog value of 52.52 versus the *Pisum sativum* (NCBI Identifier No. gi 3869255) sequence. A calculation of the percent similarity of the amino acid sequence set forth in SEQ ID NO:6 and the *Pisum sativum* sequence can be seen in Table 4. FIG. 1 presents an alignment of the amino acid sequences set forth in SEQ ID NOs:2, 4 and 6 and the *Arabidopsis thaliana, Oryza sativa* and *Pisum sativum* sequences.

TABLE 4

Percent Identity of Amino Acid Sequences Deduced From the Nucleotide Sequences of cDNA Clones Encoding Polypeptides Homologous to *Arabidopsis thaliana, Oryza sativa* and *Pisum sativum* DAD1 Proteins

| Clone | SEQ ID NO. | Percent Similarity to (Species) |
| --- | --- | --- |
| plht.pk0012.c8 | 2 | 90% (*Arabidopsis thaliana* gi 2623638) |
| cbn10.pk0058.g12 | 4 | 97% (*Oryza sativa* gi 2723473) |

TABLE 4-continued

Percent Identity of Amino Acid Sequences Deduced From the Nucleotide Sequences of cDNA Clones Encoding Polypeptides Homologous to *Arabidopsis thaliana, Oryza sativa* and *Pisum sativum* DAD1 Proteins

| Clone | SEQ ID NO. | Percent Similarity to (Species) |
| --- | --- | --- |
| A Contig composed of:<br>se1.pk0035.e10<br>ses2w.pk0011.h3<br>sdp4c.pk007.e17<br>sl1.pk0106.d1<br>sls1c.pk010.h9 | 6 | 85% (*Pisum sativum,* gi 3869255) |

Sequence alignments and percent similarity calculations were performed by the Clustal Algorithm (Higgins, D. G. et al., (1989) *CABIOS* 5(2):151–153), using the Megalign program of the LASARGENE bioinformatics computing suite (DNASTAR Inc., Madison, Wis.). Default parameters for the Clustal method for protein multiple alignments are: GAP PENALTY=10, GAP LENGTH PENALTY=10; for pairwise alignments KTUPLE 1, GAP PENALTY=3, WINDOW=5 and DIAGONALS SAVED=5. Sequence alignments and BLAST scores and probabilities indicate that the instant nucleic acid fragments encode entire DAD1 proteins. These sequences represent the first corn, *Phaseolus* and soybean sequences encoding DAD1 proteins.

Example 4

Characterization of cDNA Clones Encoding AAC-11 Homologs

The BLASTX search using the EST sequences from clones p0031.ccmba65r, p0037.crwaj44r, p0049.curar45r, p0004.cb1ha38r, p0011.cdapf47r, cbn10.pk0041.h3, cen1.pk0032.d4, p0116.cesag38r, rls24.pk0025.b4, sdp2c.pk027.j3 and src3c.pk001.j10 revealed similarity of the proteins encoded by the cDNAs to AAC-11 from *Homo sapiens* (NCBI Identifier No. gi 2623761). In the process of comparing the ESTs it was found that corn clones p0031.ccmba65r, p0037.crwaj44r, p0049.curar45r, p0004.cb1ha38r, p0011.cdapf47r, cbn10.pk0041.h3, cen1.pk0032.d4 and p0116.cesag38r had overlapping regions of homology. Soybean clones sdp2c.pk027.j3 and src3c.pk001.j10 were also found to have overlapping regions of homology. Using this homology it was possible to align the ESTs and assemble two contigs encoding unique corn and soybean AAC-11 proteins. The BLAST results for each of the contigs and the rice EST are shown in Table 5:

TABLE 5

BLAST Results for Clones Encoding Polypeptides Homologous to *Homo sapiens* AAC-11 Protein

| Clone | BLAST pLog Score |
| --- | --- |
| Contig composed of:<br>p0031.ccmba65r<br>p0037.crwaj44r<br>p0049.curar45r<br>p0004.cb1ha38r<br>p0011.cdapf47r | 37.70 |

TABLE 5-continued

BLAST Results for Clones Encoding Polypeptides
Homologous to *Homo sapiens* AAC-11 Protein

| Clone | BLAST pLog Score |
|---|---|
| cbn10.pk0041.h3 | |
| cen1.pk0032.d4 | |
| p0116.cesag38r | |
| rls24.pk0025.b4 | 5.22 |
| Contig composed of: | 16.70 |
| sdp2c.pk027.j3 | |
| src3c.pk001.j10 | |

The sequence of the corn contig composed of clones p0031.ccmba65r, p0037.crwaj44r, p0049.curar45r, p0004.cb1ha38r, p0011.cdapf47r, cbn10.pk0041.h3, cen1.pk0032.d4 and p0116.cesag38r encodes an entire AAC-11 protein and is shown in SEQ ID NO:7; the deduced amino acid sequence of this contig is shown in SEQ ID NO:8. The amino acid sequence set forth in SEQ ID NO:8 was evaluated by BLASTP, yielding a pLog value of 49.70 versus the human sequence. A calculation of the percent similarity of the amino acid sequence set forth in SEQ ID NO:8 and the *Homo sapiens* AAC-11 sequence reveals that the corn AAC-11 amino acid sequence is 21% similar to the human AAC-11 protein. FIGS. 2A and 2B present an alignment of the amino acid sequences set forth in SEQ ID NO:8 and the human AAC-11 sequence.

Sequence alignments and percent similarity calculations were performed by the Clustal Algorithm (Higgins, D. G. et al., (1989) *CABIOS* 5(2):151–153), using the Megalign program of the LASARGENE bioinformatics computing suite (DNASTAR Inc., Madison, Wis.). Default parameters for the Clustal method for protein multiple alignments are: GAP PENALTY=10, GAP LENGTH PENALTY=10; for pairwise alignments KTUPLE 1, GAP PENALTY=3, WINDOW=5 and DIAGONALS SAVED=5. Sequence alignments and BLAST scores and probabilities indicate that the instant nucleic acid-fragments encode entire DAD1 proteins.

The sequence of a portion of the cDNA insert from clone rls24.pk0025.b4 is shown in SEQ ID NO:9; the deduced amino acid sequence of this cDNA is shown in SEQ ID NO:10. The sequence of the soybean contig composed of clones sdp2c.pk027.j3 and src3c.pk001.j10 is shown in SEQ ID NO:11; the deduced amino acid sequence of this contig is shown in SEQ ID NO:12.

BLAST scores and probabilities indicate that the instant nucleic acid fragments encode entire or portions of AAC-11 proteins. These sequences represent the first plant sequences encoding AAC-11 proteins.

Example 5

Expression of Chimeric Genes in Monocot Cells

A chimeric gene comprising a cDNA encoding an apoptosis inhibitory protein in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding an apoptosis inhibitory protein, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant apoptosis inhibitory proteins in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding apoptosis inhibitory proteins. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the apoptosis inhibitory protein and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant apoptosis inhibitory proteins can be inserted into the T7 E. coli expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the apoptosis inhibitory protein are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel-electrophoresis. Gels can be observed for protein bands migrating at the expected molecular weight.

What is claimed is:

1. An isolated polynucleotide comprising:
   (a) a nucleotide sequence encoding a polypeptide having DAD1 apoptosis inhibitor activity, wherein the amino acid sequence of the polypeptide and the amino acid sequence of SEQ ID NO:6 have at least 90% sequence identity, based on the Clustal alignment method with pairwise alignment default parameters of KTUPLE=1, GAP PENALTY=3, WINDOW=5 and DIAGONALS SAVED=5, or
   (b) the full-length complement of the nucleotide sequence of (a).

2. The polynucleotide of claim 1, wherein the amino acid sequence of the polypeptide and the amino acid sequence of SEQ ID NO:6 have at least 95% sequence identity, based on the Clustal alignment method with the pairwise alignment default parameters.

3. The polynucleotide of claim 1, wherein the nucleotide sequence comprises the nucleotide sequence of SEQ ID NO:5.

4. The polynucleotide of claim 1, wherein the amino acid sequence of the polypeptide comprises the amino acid sequence of SEQ ID NO:6.

5. A vector comprising the polynucleotide of claim 1.

6. A recombinant DNA construct comprising the polynucleotide of claim 1 operably linked to at least one regulatory sequence.

7. A method for transforming a cell comprising transforming a cell with the polynucleotide of claim 1.

8. A cell comprising the recombinant DNA construct of claim 6.

9. A method for producing a transgenic plant comprising transforming a plant cell with the polynucleotide of claim 1 and regenerating a transgenic plant from the transformed plant cell.

10. A plant comprising the recombinant DNA construct of claim 6.

11. A seed comprising the recombinant DNA construct of claim 6.

12. A method for isolating a polypeptide encoded by the polynucleotide of claim 1 comprising isolating the polypeptide from a cell containing a recombinant DNA construct comprising the polynucleotide operably linked to at least one regulatory sequence, wherein the recombinant DNA construct is expressed in the cell.

* * * * *

UNITED STATES PATENT AND TRADEMARK OFFICE
CERTIFICATE OF CORRECTION

| | | |
|---|---|---|
| PATENT NO. | : 7,071,382 B2 | Page 1 of 1 |
| APPLICATION NO. | : 10/679998 | |
| DATED | : July 4, 2006 | |
| INVENTOR(S) | : Rebecca E. Cahoon et al. | |

It is certified that error appears in the above-identified patent and that said Letters Patent is hereby corrected as shown below:

Front page of patent, (75) Inventor section: please delete "Hajime Sakai, Newark, DE (US); Jennie Bih-Jien Shen, Wilmington, DE (US);".

Signed and Sealed this

Seventeenth Day of July, 2007

JON W. DUDAS
*Director of the United States Patent and Trademark Office*

SEQUENCE LISTING

<160> NUMBER OF SEQ ID NOS: 16

<210> SEQ ID NO 1
<211> LENGTH: 499
<212> TYPE: DNA
<213> ORGANISM: Phaseolus lunatus

<400> SEQUENCE: 1

```
gcgaagatct gagagaatgg cgaggtctag cagcaaggat gcacaagacc ttttccgagc      60
tctttggtct gcttatgccg caaccccccac aaatctcaag atcattgacc tctacgtcat    120
gttcgctgtt ttcaccgctc tcatccaggt agtttacatg gctttggtgg gatcatttcc    180 tttttaactcc ttcctatcag gagtactttc ttgtgtcgga actgctgttc ttgctgtttg    240
tctcaggatc caagtgaata aagagaataa ggaattcaag gatcttgcac ctgagcgagc    300
ttttgcagat tttgttctct gtaatctggt gcttcatttg gtgatcatga acttccttgg    360
ttaatttgag ttcatgtggc tgttgttggt tttgatcaaa ccttggataa taaaaagtaa    420
tagtagtata cctagacttt tgtaatagta tttatagaca gtaacttcca actaactgct    480
ttagtatttt gttgattcc                                                  499
```

<210> SEQ ID NO 2
<211> LENGTH: 115
<212> TYPE: PRT
<213> ORGANISM: Phaseolus lunatus

<400> SEQUENCE: 2

Met Ala Arg Ser Ser Ser Lys Asp Ala Gln Asp Leu Phe Arg Ala Leu

-continued

```
              1               5                  10                 15
            Trp Ser Ala Tyr Ala Ala Thr Pro Thr Asn Leu Lys Ile Ile Asp Leu
                         20                  25                 30

Tyr Val Met Phe Ala Val Phe Thr Ala Leu Ile Gln Val Val Tyr Met
                         35                  40                 45

Ala Leu Val Gly Ser Phe Pro Phe Asn Ser Phe Leu Ser Gly Val Leu
                50                      55                 60

Ser Cys Val Gly Thr Ala Val Leu Ala Val Cys Leu Arg Ile Gln Val
             65                 70                  75                 80

Asn Lys Glu Asn Lys Glu Phe Lys Asp Leu Ala Pro Glu Arg Ala Phe
                             85                  90                 95

Ala Asp Phe Val Leu Cys Asn Leu Val Leu His Leu Val Ile Met Asn
                        100                 105                110

Phe Leu Gly
                    115

<210> SEQ ID NO 3
<211> LENGTH: 712
<212> TYPE: DNA
<213> ORGANISM: Zea mays

<400> SEQUENCE: 3
gcacgagggc cgctgcccga ccccgacgcc tgctgcccag gtcttcgccg gcgacgagca      60
ctccaccaga cgagagggga ttccaagatg ccgagggcca ccagcgacgc gaagctcctg     120
atccagtccc tcggcaaggc gtacgctgcc acaccaacaa atctcaagat tattgacctc     180
tacgtgggtt ttgcggttgc cactgccctt attcaggttg cttacatggg attggttggg     240
tcgtttccct tcaactcctt cctctcagga gtcctttcat gcataggaac tgcagttctt     300
gctgtttgcc tccgcattca agtgaacaaa gacaacaaag aattcaagga ccttcccccca    360 gaaagggcct ttgctgattt cgtcctatgc aatctggtgc tccacctggt gatcatgaat     420
ttcctcggat aagcaactgc tgcaccatgt tggttaaagg ttttgtagcc ccaggttgtg     480
gtcgctgatt gttgccttta aatgtttgga actgttgtga tcgtgatgtc gaatatccat     540
atgatctgtt gaaggattac ttgtgtaagc tgagtattcc cggagggaac tattagtcga     600
atggacagtt tgcccagcgc tgagaatgtg acctagcatg ttctttattt gaagaagata     660
taattcattt ttcaaaaaaa aaaaaaaaaa aactcgaggg gggcccgtac cc             712

<210> SEQ ID NO 4
<211> LENGTH: 114
<212> TYPE: PRT
<213> ORGANISM: Zea mays

<400> SEQUENCE: 4

Met Pro Arg Ala Thr Ser Asp Ala Lys Leu Leu Ile Gln Ser Leu Gly
            1               5                  10                 15

Lys Ala Tyr Ala Ala Thr Pro Thr Asn Leu Lys Ile Ile Asp Leu Tyr
                         20                  25                 30

Val Gly Phe Ala Val Ala Thr Ala Leu Ile Gln Val Ala Tyr Met Gly
                         35                  40                 45

Leu Val Gly Ser Phe Pro Phe Asn Ser Phe Leu Ser Gly Val Leu Ser
                50                      55                 60

Cys Ile Gly Thr Ala Val Leu Ala Val Cys Leu Arg Ile Gln Val Asn
             65                 70                  75                 80

Lys Asp Asn Lys Glu Phe Lys Asp Leu Pro Pro Glu Arg Ala Phe Ala
```

```
              85                  90                  95
Asp Phe Val Leu Cys Asn Leu Val Leu His Leu Val Ile Met Asn Phe
         100                 105                 110
Leu Gly

<210> SEQ ID NO 5
<211> LENGTH: 917
<212> TYPE: DNA
<213> ORGANISM: Glycine max
<220> FEATURE:
<221> NAME/KEY: unsure
<222> LOCATION: (631)
<223> OTHER INFORMATION: n is a, c, g or t
<220> FEATURE:
<221> NAME/KEY: unsure
<222> LOCATION: (636)
<223> OTHER INFORMATION: n is a, c, g or t
<220> FEATURE:
<221> NAME/KEY: unsure
<222> LOCATION: (652)
<223> OTHER INFORMATION: n is a, c, g or t
<220> FEATURE:
<221> NAME/KEY: unsure
<222> LOCATION: (657)
<223> OTHER INFORMATION: n is a, c, g or t
<220> FEATURE:
<221> NAME/KEY: unsure
<222> LOCATION: (719)
<223> OTHER INFORMATION: n is a, c, g or t
<220> FEATURE:
<221> NAME/KEY: unsure
<222> LOCATION: (785)
<223> OTHER INFORMATION: n is a, c, g or t
<220> FEATURE:
<221> NAME/KEY: unsure
<222> LOCATION: (843)
<223> OTHER INFORMATION: n is a, c, g or t
<220> FEATURE:
<221> NAME/KEY: unsure
<222> LOCATION: (849)
<223> OTHER INFORMATION: n is a, c, g or t
<220> FEATURE:
<221> NAME/KEY: unsure
<222> LOCATION: (859)..(860)
<223> OTHER INFORMATION: n is a, c, g or t
<220> FEATURE:
<221> NAME/KEY: unsure
<222> LOCATION: (886)
<223> OTHER INFORMATION: n is a, c, g or t
<220> FEATURE:
<221> NAME/KEY: unsure
<222> LOCATION: (890)
<223> OTHER INFORMATION: n is a, c, g or t
<220> FEATURE:
<221> NAME/KEY: unsure
<222> LOCATION: (897)
<223> OTHER INFORMATION: n is a, c, g or t
<220> FEATURE:
<221> NAME/KEY: unsure
<222> LOCATION: (906)
<223> OTHER INFORMATION: n is a, c, g or t

<400> SEQUENCE: 5
ggcaaatcgc gaagactaga tctgatctga gagaatggct cctcggtcta gcagcaagga      60
cgcccaagac cttttccgcg ctctttggtc tgcttatgct gcaaccccca ctaatctcaa     120
gatcattgat ctctatgtca tctatgccgt attcaccgct ttcatccagg ttgtttacat     180
ggctttggtt ggatcatttc catttaactc cttcctatca ggagtacttt cttgtgtagg     240
aactgctgtt cttgctgttt gtctcaggat ccaagtgaat aaagagaata aggaattcaa     300
ggatcttgca cctgagcgcg cttttgcgga ttttgttctc tgtaatttgg tgcttcattt     360
```

-continued

```
ggtgatcatg aacttccttg gttaaattgg gtttgtgtgg cggttgttgt ttctgattga    420
acccttcgat aataaaaatt aaatagtagt atacctagac ttttgtaata gtatttatag    480
acagtagccg gcattctact aattgctttg gctttatgtt gattacccc acctcccatt     540 tttgggttcc ctgttttgaa cgaagagatt ttgccatctt ttgaagttta aagtactttt    600
gaatggcgaa ataagaagg attgttatta naaaanaaaa aaaataaca anatataac       660 gcttacattt aagtggcact ttcggggaaa tgtgcgcgga accctattgt taatttccna    720
aatacatcaa atagtaccgc caagaacata accctgataa agctcataat atgaaaagga    780
gatanatatc acattcgtgt cgcctaaccc ttttgcggat ttgcctcccg gttttgccaa    840
canaacccng gaaataaann gcgaaatact ggtgccaatg gtaacnatgn ttcaaangga    900
aatctnaaat tcccaag                                                   917
```

<210> SEQ ID NO 6
<211> LENGTH: 116
<212> TYPE: PRT
<213> ORGANISM: Glycine max

<400> SEQUENCE: 6

```
Met Ala Pro Arg Ser Ser Ser Lys Asp Ala Gln Asp Leu Phe Arg Ala
1               5                   10                  15

Leu Trp Ser Ala Tyr Ala Ala Thr Pro Thr Asn Leu Lys Ile Ile Asp
            20                  25                  30

Leu Tyr Val Ile Tyr Ala Val Phe Thr Ala Phe Ile Gln Val Val Tyr
        35                  40                  45

Met Ala Leu Val Gly Ser Phe Pro Phe Asn Ser Phe Leu Ser Gly Val
    50                  55                  60

Leu Ser Cys Val Gly Thr Ala Val Leu Ala Val Cys Leu Arg Ile Gln
65                  70                  75                  80

Val Asn Lys Glu Asn Lys Glu Phe Lys Asp Leu Ala Pro Glu Arg Ala
                85                  90                  95

Phe Ala Asp Phe Val Leu Cys Asn Leu Val Leu His Leu Val Ile Met
            100                 105                 110

Asn Phe Leu Gly
        115
```

<210> SEQ ID NO 7
<211> LENGTH: 2671
<212> TYPE: DNA
<213> ORGANISM: Zea mays
<220> FEATURE:
<221> NAME/KEY: unsure
<222> LOCATION: (690)
<223> OTHER INFORMATION: n is a, c, g or t
<220> FEATURE:
<221> NAME/KEY: unsure
<222> LOCATION: (2161)
<223> OTHER INFORMATION: n is a, c, g or t
<220> FEATURE:
<221> NAME/KEY: unsure
<222> LOCATION: (2180)
<223> OTHER INFORMATION: n is a, c, g or t

<400> SEQUENCE: 7

```
gcatcccttc ccagttctgt ccctctcgaa ccctaactcc aaaaaccctc gctctcctct     60
catggccgcc gccgcagctg acgacgcagc cgaggtggag cggctttacg agctcggcga    120
gcgcctctcc tccgccaatg acaagtccga gcatgcggcg gactacgagg cgattattgc    180
agcggtgaag ggacagagtg ccaaggcgaa gcagctcgca gcgcagctta tccccaggtt    240
```

-continued

```
cttccggagc ttccctgcac tcggcacgcg cgccatgtca gccatgttcg atctcgtcga    300
tatggaggag ctcgcgatca gaatacaagc tattcgtggc tttccacttc ttggcaaaga    360
tactgaattt gtgtcaaaaa ttgcagatgt tttgggtcag ctccttacaa gcgaggaaaa    420
tgttgagcgt gatgctgttc ataaagcgct catgtccctt atacggcaag atgttaaaaa    480
ttcattacaa cctttattta agcatgtgga gcaaggatca gagattcgtg agaagattat    540
ttgttttctt cgagacaagg tctttcctct aaagcagag ctgctgaaac ctcaagcaga     600
aatggagaga tttataacgg atttgataaa gaaaagtgtg caagatgtaa ctggttcaga    660
attcgaacta ttcatggggt tcttgcgaan ttggagcata tttggggatt ctgctcctag    720
agagtccttt caagaactaa ttgaaattat tcaagcacag gctgatctga attcacaatt    780
caacgtttct gacattgacc acattgagag gtggatttca tgcatgtata tggctcttcc    840
gatcttcatg agaggagcat cagcaagcaa gttcctcaat tacttcgtta agcaaattgt    900
tccagcattc gagaagattc ctgaagaaaa gaaactggat ttgctcaaga ctattgcttc    960
aagttcaccg tacgcgacag ctcaagattc acgtcagctg cttccatctg ttgttcagtt   1020
actcaacaaa tatatgcctg ggaagaaggt ggacgatatc aaccataatt atgttgaatg   1080
cttgctgtac acttatcatc atttggctca taagactcca aacacaacga acagtctatg   1140
tggttacaag attgttactg ggcaaccatc ggatagactt ggagaggact tcacagagca   1200
ttacaaagat tttacagaga ggttaactgg aacagaagag acggtaagag cagcctcaaa   1260
gcgactaact cagggaatgg cagatttcag caaggcaata tcttcagcaa aaaccgaaga   1320
ggaaaaaact aaaattaaag gcgatcaaca aacttcaaca aggacaatga ggtcatataa   1380
caatatattg gcaatgacac agtcattgca ttcaaaatcc cctttattta tcggtgataa   1440
gaaaatcact ctgtcatgga tggagcagcc caacaaagca gcagctacga agcagggg    1500
gaagaggtca caacctagta caaatgggaa tgaccctgca acaagaagg ggagaggagg    1560
aatgcaaaac cagctagtga acagagcttt tgaaggactg tctcatgttg aagaggcag    1620
tggaagaggt cggggcaagg gtgggccgag gaagaggaag aggatggagt ggggtaccac   1680
tgagatgacc tggaaattat gttcaaacct gacaagggat gagctttctg cttccaccag   1740
agagtaaact ccaaggtcga tgttttattg gtgtgcatta ctgcaacgcg ttgaaatgga   1800
tcaaggcaca caacagcaga aatgcgtaca cagagaaagg atgctaagaa atatctgcaa   1860
gtttgtgcat ctttcttatc catttaccat ctcatcgtgt tctttgccac cctaaccgtc   1920
gtgtcacctg cgttggctgg ctgtttgatg aactgggcag ttcgatatct tgttctttta   1980
ttttatttta cagtgtttga agagacgacc aagcttgtgc tgactttgtt tgagttcgtt   2040
ttatgtttcg tccttgtact gacacagatg tattagtgat gtttaacttt tatgtaacga   2100
ttgattagct gtaatataag ttaagcattt aataagctat ttaaaaaaa aaaaaaaacc    2160
nkrcgggatt ggagttgggn cccactgagg atgaccttgg aaatttattg ttcaaaacct   2220
tgaccaaggg gatgagcttt ctgcttccac cagagagtaa actccaaggt cgatgttttta  2280
ttggtgtgca ttactgcaac gcgttgaaat ggatcaaggc acacaacagc agaaatgcgt   2340
acacagagaa aggatgctaa gaaatatctg caagtttgtg catctttctt atccatttac   2400
catctcatcg tgttctttgc caccctaacc gtcgtgtcac ctgcgttggc tggctgtttg   2460
atgaactggg cagttcgata tcttgttcct ttattttatt ttacagtgtt tgaagagacg   2520
accaagcttg tgctgacttt gtttgagttc gttttatgtt tcgtccttgt actgacacag   2580
```

-continued

```
atgtattagt gatgtttaac ttttatgtaa cgattgatta gctgtaatat aagttaagca    2640
tttaataagc tatttaaaaa aaaaaaaaaa a                                   2671
```

<210> SEQ ID NO 8
<211> LENGTH: 561
<212> TYPE: PRT
<213> ORGANISM: Zea mays
<220> FEATURE:
<221> NAME/KEY: UNSURE
<222> LOCATION: (210)
<223> OTHER INFORMATION: Xaa can be any naturally occurring amino acid
<220> FEATURE:
<221> NAME/KEY: UNSURE
<222> LOCATION: (523)
<223> OTHER INFORMATION: Xaa can be any naturally occurring amino acid
<220> FEATURE:
<221> NAME/KEY: UNSURE
<222> LOCATION: (526)
<223> OTHER INFORMATION: Xaa can be any naturally occurring amino acid

<400> SEQUENCE: 8

```
Met Ala Ala Ala Ala Asp Asp Ala Ala Glu Val Glu Arg Leu Tyr
1               5                   10                  15

Glu Leu Gly Glu Arg Leu Ser Ser Ala Asn Asp Lys Ser Glu His Ala
            20                  25                  30

Ala Asp Tyr Glu Ala Ile Ile Ala Ala Val Lys Gly Gln Ser Ala Lys
        35                  40                  45

Ala Lys Gln Leu Ala Ala Gln Leu Ile Pro Arg Phe Phe Arg Ser Phe
    50                  55                  60

Pro Ala Leu Gly Thr Arg Ala Met Ser Ala Met Phe Asp Leu Val Asp
65                  70                  75                  80

Met Glu Glu Leu Ala Ile Arg Ile Gln Ala Ile Arg Gly Phe Pro Leu
                85                  90                  95

Leu Gly Lys Asp Thr Glu Phe Val Ser Lys Ile Ala Asp Val Leu Gly
            100                 105                 110

Gln Leu Leu Thr Ser Glu Glu Asn Val Glu Arg Asp Ala Val His Lys
        115                 120                 125

Ala Leu Met Ser Leu Ile Arg Gln Asp Val Lys Asn Ser Leu Gln Pro
    130                 135                 140

Leu Phe Lys His Val Glu Gln Gly Ser Glu Ile Arg Glu Lys Ile Ile
145                 150                 155                 160

Cys Phe Leu Arg Asp Lys Val Phe Pro Leu Lys Ala Glu Leu Leu Lys
                165                 170                 175

Pro Gln Ala Glu Met Glu Arg Phe Ile Thr Asp Leu Ile Lys Lys Ser
            180                 185                 190

Val Gln Asp Val Thr Gly Ser Glu Phe Glu Leu Phe Met Gly Phe Leu
        195                 200                 205

Arg Xaa Trp Ser Ile Phe Gly Asp Ser Ala Pro Arg Glu Ser Phe Gln
    210                 215                 220

Glu Leu Ile Glu Ile Ile Gln Ala Gln Ala Asp Leu Asn Ser Gln Phe
225                 230                 235                 240

Asn Val Ser Asp Ile Asp His Ile Glu Arg Trp Ile Ser Cys Met Tyr
                245                 250                 255

Met Ala Leu Pro Ile Phe Met Arg Gly Ala Ser Ala Ser Lys Phe Leu
            260                 265                 270

Asn Tyr Phe Val Lys Gln Ile Val Pro Ala Phe Glu Lys Ile Pro Glu
        275                 280                 285

Glu Lys Lys Leu Asp Leu Leu Lys Thr Ile Ala Ser Ser Ser Pro Tyr
```

```
                290                 295                 300
Ala Thr Ala Gln Asp Ser Arg Gln Leu Leu Pro Ser Val Val Gln Leu
305                 310                 315                 320

Leu Asn Lys Tyr Met Pro Gly Lys Lys Val Asp Asp Ile Asn His Asn
                325                 330                 335

Tyr Val Glu Cys Leu Leu Tyr Tyr His His Leu Ala His Lys Thr
                340                 345                 350

Pro Asn Thr Thr Asn Ser Leu Cys Gly Tyr Lys Ile Val Thr Gly Gln
                355                 360                 365

Pro Ser Asp Arg Leu Gly Glu Asp Phe Thr Glu His Tyr Lys Asp Phe
370                 375                 380

Thr Glu Arg Leu Thr Gly Thr Glu Thr Val Arg Ala Ala Ser Lys
385                 390                 395                 400

Arg Leu Thr Gln Gly Met Ala Asp Phe Ser Lys Ala Ile Ser Ser Ala
                405                 410                 415

Lys Thr Glu Glu Lys Thr Lys Ile Lys Gly Asp Gln Gln Thr Ser
                420                 425                 430

Thr Arg Thr Met Arg Ser Tyr Asn Asn Ile Leu Ala Met Thr Gln Ser
                435                 440                 445

Leu His Ser Lys Ser Pro Leu Phe Ile Gly Asp Lys Lys Ile Thr Leu
                450                 455                 460

Ser Trp Met Glu Gln Pro Asn Lys Ala Ala Thr Lys Ala Gly Gly
465                 470                 475                 480

Lys Arg Ser Gln Pro Ser Thr Asn Gly Asn Asp Pro Ala Asn Lys Lys
                485                 490                 495

Gly Arg Gly Gly Met Gln Asn Gln Leu Val Asn Arg Ala Phe Glu Gly
                500                 505                 510

Leu Ser His Val Gly Arg Gly Ser Gly Arg Xaa Arg Gly Xaa Gly Gly
                515                 520                 525

Pro Arg Lys Arg Lys Arg Met Glu Trp Gly Thr Thr Glu Met Thr Trp
530                 535                 540

Lys Leu Cys Ser Asn Leu Thr Arg Asp Glu Leu Ser Ala Ser Thr Arg
545                 550                 555                 560

Glu

<210> SEQ ID NO 9
<211> LENGTH: 556
<212> TYPE: DNA
<213> ORGANISM: Oryza sativa
<220> FEATURE:
<221> NAME/KEY: unsure
<222> LOCATION: (179)
<223> OTHER INFORMATION: n is a, c, g or t
<220> FEATURE:
<221> NAME/KEY: unsure
<222> LOCATION: (339)
<223> OTHER INFORMATION: n is a, c, g or t
<220> FEATURE:
<221> NAME/KEY: unsure
<222> LOCATION: (345)
<223> OTHER INFORMATION: n is a, c, g or t
<220> FEATURE:
<221> NAME/KEY: unsure
<222> LOCATION: (368)
<223> OTHER INFORMATION: n is a, c, g or t
<220> FEATURE:
<221> NAME/KEY: unsure
<222> LOCATION: (390)
<223> OTHER INFORMATION: n is a, c, g or t
<220> FEATURE:
<221> NAME/KEY: unsure
```

<222> LOCATION: (392)
<223> OTHER INFORMATION: n is a, c, g or t
<220> FEATURE:
<221> NAME/KEY: unsure
<222> LOCATION: (427)
<223> OTHER INFORMATION: n is a, c, g or t
<220> FEATURE:
<221> NAME/KEY: unsure
<222> LOCATION: (434)
<223> OTHER INFORMATION: n is a, c, g or t
<220> FEATURE:
<221> NAME/KEY: unsure
<222> LOCATION: (464)
<223> OTHER INFORMATION: n is a, c, g or t
<220> FEATURE:
<221> NAME/KEY: unsure
<222> LOCATION: (472)
<223> OTHER INFORMATION: n is a, c, g or t
<220> FEATURE:
<221> NAME/KEY: unsure
<222> LOCATION: (496)
<223> OTHER INFORMATION: n is a, c, g or t
<220> FEATURE:
<221> NAME/KEY: unsure
<222> LOCATION: (518)
<223> OTHER INFORMATION: n is a, c, g or t
<220> FEATURE:
<221> NAME/KEY: unsure
<222> LOCATION: (524)
<223> OTHER INFORMATION: n is a, c, g or t
<220> FEATURE:
<221> NAME/KEY: unsure
<222> LOCATION: (534)
<223> OTHER INFORMATION: n is a, c, g or t
<220> FEATURE:
<221> NAME/KEY: unsure
<222> LOCATION: (551)
<223> OTHER INFORMATION: n is a, c, g or t

<400> SEQUENCE: 9

```
ggcatactaa cccccccaaa tctcccacac cgctcccccg ccgccatggc cgcctccgac      60
gccgacgccg cggaggtcga gcggctctac gagctcggcg agcgcctctc ctccgccaag     120
gacaagtccc agcacgcggc ggactacgag gcgatcatat cggccgtgaa ggggcaganc     180
gtgaaggcga agcagctcgc ggcgcagctc atccccgct tcttccggag cttcccggca      240
ctcgccccgc gcgccatgga ggccatgttc gacctcgtcg acatggatga actcgcgact     300
agaatacaac tattcgtggg ttttcacttc ttgccaaana tgcanaattt gtctcaaaaa     360
ttgccganat ccttggacaa tccttgcaan tnaggaaaat gtggacgtga tgctgtcata    420
aagcacngat gtcncttata cggcaggatt taaaattctt gcancttatt angattggat    480
tcgggatata attctnaaaa ttattgttcc taagaaangc tccngtaaag aaantgtgaa   540
ctcaacagag ngaaat                                                    556
```

<210> SEQ ID NO 10
<211> LENGTH: 131
<212> TYPE: PRT
<213> ORGANISM: Oryza sativa
<220> FEATURE:
<221> NAME/KEY: UNSURE
<222> LOCATION: (45)
<223> OTHER INFORMATION: Xaa can be any naturally occurring amino acid
<220> FEATURE:
<221> NAME/KEY: UNSURE
<222> LOCATION: (98)
<223> OTHER INFORMATION: Xaa can be any naturally occurring amino acid
<220> FEATURE:
<221> NAME/KEY: UNSURE
<222> LOCATION: (100)
<223> OTHER INFORMATION: Xaa can be any naturally occurring amino acid
<220> FEATURE:

```
<221> NAME/KEY: UNSURE
<222> LOCATION: (108)
<223> OTHER INFORMATION: Xaa can be any naturally occurring amino acid
<220> FEATURE:
<221> NAME/KEY: UNSURE
<222> LOCATION: (115)..(116)
<223> OTHER INFORMATION: Xaa can be any naturally occurring amino acid
<220> FEATURE:
<221> NAME/KEY: UNSURE
<222> LOCATION: (128)
<223> OTHER INFORMATION: Xaa can be any naturally occurring amino acid
<220> FEATURE:
<221> NAME/KEY: UNSURE
<222> LOCATION: (130)
<223> OTHER INFORMATION: Xaa can be any naturally occurring amino acid

<400> SEQUENCE: 10

Met Ala Ser Asp Ala Asp Ala Ala Glu Val Glu Arg Leu Tyr Glu
 1               5                  10                  15

Leu Gly Glu Arg Leu Ser Ser Ala Lys Asp Lys Ser Gln His Ala Ala
            20                  25                  30

Asp Tyr Glu Ala Ile Ile Ser Ala Val Lys Gly Gln Xaa Val Lys Ala
        35                  40                  45

Lys Gln Leu Ala Ala Gln Leu Ile Pro Arg Phe Phe Arg Ser Phe Pro
    50                  55                  60

Ala Leu Ala Pro Arg Ala Met Glu Ala Met Phe Asp Leu Val Asp Met
65                  70                  75                  80

Asp Glu Leu Ala Thr Arg Ile Gln Leu Phe Val Gly Phe His Phe Leu
                85                  90                  95

Pro Xaa Met Xaa Asn Leu Ser Gln Lys Leu Pro Xaa Ser Leu Asp Asn
           100                 105                 110

Pro Cys Xaa Xaa Gly Lys Cys Gly Arg Asp Ala Val Ile Lys His Xaa
           115                 120                 125

Cys Xaa Leu
    130

<210> SEQ ID NO 11
<211> LENGTH: 749
<212> TYPE: DNA
<213> ORGANISM: Glycine max
<220> FEATURE:
<221> NAME/KEY: unsure
<222> LOCATION: (678)
<223> OTHER INFORMATION: n is a, c, g or t
<220> FEATURE:
<221> NAME/KEY: unsure
<222> LOCATION: (724)
<223> OTHER INFORMATION: n is a, c, g or t
<220> FEATURE:
<221> NAME/KEY: unsure
<222> LOCATION: (745)
<223> OTHER INFORMATION: n is a, c, g or t

<400> SEQUENCE: 11
gcgctggcta ctgtttatag tttactgtaa actgtgttta cgttgtgtcg tgtggcgtgt    60
tcagtgaggt aagggaaact cgtccccatc gaagagctta cttgacctcg caccacggaa   120
tcgttcccta ctaattcaac tcaacaacac tatcgtctcc attcactagt tagaaacgtg   180
cgttccaatg tctgatcctg ccgaagaggc tgctttcatc gagaagctct acgaatacgg   240
cgagcaactc aacaacacta tcgtctccat tcactagtta gaaacgtgcg ttccaatgtc   300
tgatcctgcc gaagaggctg ctttcatcga gaagctctac gaatacgcg agcaactcaa   360 caatgccaag gacaagtcgc agaatgtgca ggattaccag ggaatcatag atgcggcgaa   420
```

-continued

```
gacgagtgtg aaggcgaagc agctcgctgc acagctgatt cccaggttct acaagttctt    480
tcctgacctt tctagccctg ctctcgatgc acatcttgat ttggttgagg ctgaagaact    540
cggggttcga gtgcaagcaa ttagaggtct gcctcttttt tgtaaggata cacctgagaa    600
tattgggaag atggttgata ttcttgtgca aattcttggg tctgaggaat ttgtggagcg    660
tgatgcagta cataaggntc ttaagtcctt tgctgaggca aggatgtcaa aagcttcctt    720
gacngctttg ttaagcacaa ttggnaagg                                      749
```

<210> SEQ ID NO 12
<211> LENGTH: 131
<212> TYPE: PRT
<213> ORGANISM: Glycine max
<220> FEATURE:
<221> NAME/KEY: UNSURE
<222> LOCATION: (128)
<223> OTHER INFORMATION: Xaa can be any naturally occurring amino acid

<400> SEQUENCE: 12

```
Met Ser Asp Pro Ala Glu Glu Ala Ala Phe Ile Glu Lys Leu Tyr Glu
1               5                   10                  15

Tyr Gly Glu Gln Leu Asn Asn Ala Lys Asp Lys Ser Gln Asn Val Gln
            20                  25                  30

Asp Tyr Gln Gly Ile Ile Asp Ala Ala Lys Thr Ser Val Lys Ala Lys
        35                  40                  45

Gln Leu Ala Ala Gln Leu Ile Pro Arg Phe Tyr Lys Phe Phe Pro Asp
    50                  55                  60

Leu Ser Ser Pro Ala Leu Asp Ala His Leu Asp Leu Val Glu Ala Glu
65                  70                  75                  80

Glu Leu Gly Val Arg Val Gln Ala Ile Arg Gly Leu Pro Leu Phe Cys
                85                  90                  95

Lys Asp Thr Pro Glu Asn Ile Gly Lys Met Val Asp Ile Leu Val Gln
            100                 105                 110

Ile Leu Gly Ser Glu Glu Phe Val Glu Arg Asp Ala Val His Lys Xaa
        115                 120                 125

Leu Lys Ser
    130
```

<210> SEQ ID NO 13
<211> LENGTH: 115
<212> TYPE: PRT
<213> ORGANISM: Arabidopsis thaliana

<400> SEQUENCE: 13

```
Met Val Lys Ser Thr Ser Lys Asp Ala Gln Asp Leu Phe His Ser Leu
1               5                   10                  15

His Ser Ala Tyr Thr Ala Thr Pro Thr Asn Leu Lys Ile Ile Asp Leu
            20                  25                  30

Tyr Val Cys Phe Ala Val Phe Thr Ala Leu Ile Gln Val Ala Tyr Met
        35                  40                  45

Ala Leu Val Gly Ser Phe Pro Phe Asn Ser Phe Leu Ser Gly Val Leu
    50                  55                  60

Ser Cys Ile Gly Thr Ala Val Leu Ala Val Cys Leu Arg Ile Gln Val
65                  70                  75                  80

Asn Lys Glu Asn Lys Glu Phe Lys Asp Leu Ala Pro Glu Arg Ala Phe
                85                  90                  95

Ala Asp Phe Val Leu Cys Asn Leu Val Leu His Leu Val Ile Ile Asn
            100                 105                 110
```

```
Phe Leu Gly
        115

<210> SEQ ID NO 14
<211> LENGTH: 114
<212> TYPE: PRT
<213> ORGANISM: Oryza sativa

<400> SEQUENCE: 14

Met Pro Arg Ala Thr Ser Asp Ala Lys Leu Leu Ile Gln Ser Leu Gly
 1               5                  10                  15

Lys Ala Tyr Ala Ala Thr Pro Thr Asn Leu Lys Ile Ile Asp Leu Tyr
            20                  25                  30

Val Val Phe Ala Val Ala Thr Ala Leu Ile Gln Val Val Tyr Met Gly
        35                  40                  45

Ile Val Gly Ser Phe Pro Phe Asn Ser Phe Leu Ser Gly Val Leu Ser
    50                  55                  60

Cys Ile Gly Thr Ala Val Leu Ala Val Cys Leu Arg Ile Gln Val Asn
65                  70                  75                  80

Lys Asp Asn Lys Glu Phe Lys Asp Leu Pro Pro Glu Arg Ala Phe Ala
                85                  90                  95

Asp Phe Val Leu Cys Asn Leu Val Leu His Leu Val Ile Met Asn Phe
            100                 105                 110

Leu Gly

<210> SEQ ID NO 15
<211> LENGTH: 117
<212> TYPE: PRT
<213> ORGANISM: Pisum sativum

<400> SEQUENCE: 15

Met Ala Lys Thr Ser Ser Thr Thr Lys Asp Ala Gln Asp Leu Phe His
 1               5                  10                  15

Ala Ile Trp Ser Ala Tyr Ser Ala Thr Pro Thr Asn Leu Lys Ile Ile
            20                  25                  30

Asp Leu Tyr Val Val Phe Ala Val Phe Thr Ala Leu Leu Gln Asp Val
        35                  40                  45

Tyr Met Ala Leu Val Gly Pro Phe Pro Phe Asn Ser Phe Leu Ser Gly
    50                  55                  60

Val Leu Ser Cys Val Gly Thr Ala Val Leu Ala Val Cys Leu Arg Ile
65                  70                  75                  80

Gln Val Asn Lys Glu Asn Lys Glu Phe Lys Asp Leu Gly Pro Glu Arg
                85                  90                  95

Ala Phe Ala Asp Phe Val Leu Cys Asn Leu Val Leu His Leu Val Ile
            100                 105                 110

Met Asn Phe Leu Gly
        115

<210> SEQ ID NO 16
<211> LENGTH: 528
<212> TYPE: PRT
<213> ORGANISM: Homo sapiens

<400> SEQUENCE: 16

Met Gly Leu Ser Leu Thr Met Pro Thr Val Glu Glu Leu Tyr Arg Asn
 1               5                  10                  15

Tyr Gly Ile Leu Ala Asp Ala Thr Glu Gln Val Gly Gln His Lys Asp
```

-continued

```
                    20                  25                  30
Ala Tyr Gln Val Ile Leu Asp Gly Val Lys Gly Gly Thr Lys Glu Lys
         35                  40                  45

Arg Leu Ala Ala Gln Phe Ile Pro Lys Phe Phe Lys His Phe Pro Glu
         50                  55                  60

Leu Ala Asp Ser Ala Ile Asn Ala Gln Leu Asp Leu Cys Glu Asp Glu
 65                  70                  75                  80

Asp Val Ser Ile Arg Arg Gln Ala Ile Lys Glu Leu Pro Gln Phe Ala
                 85                  90                  95

Thr Gly Glu Asn Leu Pro Arg Val Ala Asp Ile Leu Thr Gln Leu Leu
                 100                 105                 110

Gln Thr Asp Asp Ser Ala Glu Phe Asn Leu Val Asn Asn Ala Leu Leu
         115                 120                 125

Ser Ile Phe Lys Met Asp Ala Lys Gly Thr Leu Gly Gly Leu Phe Ser
         130                 135                 140

Gln Ile Leu Gln Gly Glu Asp Ile Val Arg Glu Arg Ala Ile Lys Phe
145                 150                 155                 160

Leu Ser Thr Lys Leu Lys Thr Leu Pro Asp Glu Val Leu Thr Lys Glu
                 165                 170                 175

Val Glu Glu Leu Ile Leu Thr Glu Ser Lys Lys Val Leu Glu Asp Val
                 180                 185                 190

Thr Gly Glu Glu Phe Val Leu Phe Met Lys Ile Leu Ser Gly Leu Lys
         195                 200                 205

Ser Leu Gln Thr Val Ser Gly Arg Gln Gln Leu Val Glu Leu Val Ala
         210                 215                 220

Glu Gln Ala Asp Leu Glu Gln Thr Phe Asn Pro Ser Asp Pro Asp Cys
225                 230                 235                 240

Val Asp Arg Leu Leu Gln Cys Thr Arg Gln Ala Val Pro Leu Phe Ser
                 245                 250                 255

Lys Asn Val His Ser Thr Arg Phe Val Thr Tyr Phe Cys Glu Gln Val
                 260                 265                 270

Leu Pro Asn Leu Gly Thr Leu Thr Thr Pro Val Glu Gly Leu Asp Ile
         275                 280                 285

Gln Leu Glu Val Leu Lys Leu Leu Ala Glu Met Ser Ser Phe Cys Gly
         290                 295                 300

Asp Met Glu Lys Leu Glu Thr Asn Leu Arg Lys Leu Phe Asp Lys Leu
305                 310                 315                 320

Leu Glu Tyr Met Pro Leu Pro Pro Glu Glu Ala Glu Asn Gly Glu Asn
                 325                 330                 335

Ala Gly Asn Glu Glu Pro Lys Leu Gln Phe Ser Tyr Val Glu Cys Leu
                 340                 345                 350

Leu Tyr Ser Phe His Gln Leu Gly Arg Lys Leu Pro Asp Phe Leu Thr
         355                 360                 365

Ala Lys Leu Asn Ala Glu Lys Leu His Glu Ser Lys Ile Arg Leu Gln
         370                 375                 380

Tyr Phe Ala Arg Gly Leu Gln Val Tyr Ile Arg Gln Leu Arg Leu Ala
385                 390                 395                 400

Leu Gln Gly Lys Thr Gly Glu Ala Leu Lys Thr Glu Glu Asn Lys Ile
                 405                 410                 415

Lys Val Val Ala Leu Lys Ile Thr Asn Asn Ile Asn Val Leu Ile Lys
                 420                 425                 430

Asp Leu Phe His Ile Pro Pro Ser Tyr Lys Ser Thr Val Thr Leu Ser
         435                 440                 445
```

```
Trp Lys Pro Val Gln Lys Val Glu Ile Gly Gln Lys Arg Ala Ser Glu
    450             455             460

Asp Thr Thr Ser Gly Ser Pro Pro Lys Lys Ser Ser Ala Gly Pro Lys
465             470             475             480

Arg Met Pro Gly Arg Phe Ile Thr Leu Pro Val Gly Asn Ile Ala Ala
                485             490             495

Ile Trp Ala Thr Leu Ile Met Arg Gly Ala Phe Arg Gly Ser Lys Trp
            500             505             510

Pro Arg Leu Gly His Thr Lys Glu Ile Val Val Gly Glu Arg Leu Tyr
        515             520             525
```